United States Patent [19]
Kotwal et al.

[11] Patent Number: 5,151,509
[45] Date of Patent: Sep. 29, 1992

[54] GENE ENCODING SERINE PROTEASE INHIBITOR

[75] Inventors: Girish J. Kotwal; Bernard Moss, both of Bethesda, Md.

[73] Assignee: United States of America, Washington, D.C.

[21] Appl. No.: 285,510

[22] Filed: Dec. 16, 1988

[51] Int. Cl.[5] .............................................. C12N 15/15
[52] U.S. Cl. .................................... 536/27; 435/69.2; 935/10
[58] Field of Search .................... 435/69.2, 183, 172.3, 435/320.1; 536/27; 935/14, 10, 9

[56] References Cited

PUBLICATIONS

Boursnell et al. J Gen Virol. 69:2995 (1988).
Pickup et al. PNAS, 83:7698 (1986).
Niles et al. Virology 153(1):96 (1986).
Kotwal et al., "Vaccinia Virus Encodes Two Proteins That Are Structurally Related to Members of the Plasma Serine Protease Inhibitor Superfamily", Journal of Virology, Feb. 1989, vol. 63 No. 2, pp. 600–606.

Primary Examiner—Richard A. Schwartz
Assistant Examiner—John LeGuyader
Attorney, Agent, or Firm—Townsend and Townsend

[57] ABSTRACT

Novel serine protease inhibitors and genes encoding the same are described.

2 Claims, 34 Drawing Sheets

```
          GTTAAGTATGAATACGGGGTACAAACATAAACTGAAGTTTAACATTATTTATTTATGATATATAT

40► M  D  I  F  K  E  L  I  L  K  H  T  D  E  N
          CGTTATTGTTTGGTCTATACCATGGATATCTTTAAAGAACTAATCTTAAAACACACGGATGAAAA

V  L  I  S  P  V  S  I  L  S  T  L  S  I  L  N  H  G  A  A  G
          TGTTTTGATTTCTCCAGTTTCTATTTTATCTACTTTATCTATTCTAAATCATGGAGGAGCTGGTT

S  T  A  E  Q  L  S  K  Y  I  E  N  M  N  E  N  T  P  D  D  N  N
          CTACAGCTGAACAACTATCAAAATATATAGAGAATATGAATGAGAATACACCCGATGACAATAAT

D  M  D  V  D  I  P  Y  C  A  T  L  A  T  A  N  K  I  Y  G  S  D
          GACATGGACGTAGATATTCCGTATTGTGCGACACTAGCTACCGCAAATAAAATATACGGTAGCGA

S  I  E  F  H  A  S  F  L  Q  K  I  K  D  D  F  Q  T  V  N  F
          TAGTATCGAGTTCCACGCCTCCTTCCTACAAAAAATAAAAGACGATTTTCAAACTGTAAACTTTA

N  N  A  N  Q  T  K  E  L  I  N  E  W  V  K  T  M  T  N  G  K  I
          ATAATGCTAACCAAACAAAGGAACTAATCAACGAATGGGTTAAGACAATGACAAATGGTAAAATT

N  S  L  L  T  S  P  L  S  I  N  T  R  M  T  V  V  S  A  V  H  F
          AATTCCTTATTGACTAGTCCGCTATCCATTAATACTCGTATGACAGTTGTTAGCGCCGTCCATTT

K  A  M  W  K  Y  P  F  S  K  H  L  T  Y  T  D  K  F  Y  I  S
          TAAAGCAATGTGGAAATATCCATTTTCTAAACATCTTACATATACAGACAAGTTTTATATTTCTA

K  N  I  V  T  S  V  D  M  M  V  S  T  E  N  N  L  Q  Y  V  H  I
          AGAATATAGTTACCAGTGTTGATATGATGGTGAGCACTGAGAATAACTTGCAATATGTACATATT

N  E  L  F  G  G  F  S  I  I  D  I  P  Y  E  G  N  S  S  M  V  I
          AATGAATTATTCGGAGGATTCTCTATTATCGATATTCCATACGAGGGAAACTCTAGTATGGTAAT

I  L  P  D  D  I  E  G  I  Y  N  I  E  K  N  I  T  D  E  K  F
          TATACTACCGGACGACATAGAAGGTATATATAACATAGAAAAAAATATAACAGATGAAAAATTTA

K  K  W  C  G  M  L  S  T  K  S  I  D  L  Y  M  P  K  F  K  V  E
          AAAAATGGTGTGGTATGTTATCTACTAAAAGTATAGACTTGTATATGCCAAAGTTTAAAGTGGAA

M  T  E  P  Y  N  L  V  P  I  L  E  N  L  G  L  T  N  I  F  G  Y
          ATGACAGAACCGTATAATCTGGTACCGATTTTAGAAAATTTAGGACTTACTAATATATTCGGATA

Y  A  D  F  S  K  M  C  N  E  T  I  T  V  E  K  F  L  H  T  T
          TTATGCAGATTTTAGCAAGATGTGTAATGAAACTATCACTGTAGAAAAATTTCTACATACGACGT

F  I  D  V  N  E  E  Y  T  E  A  S  A  V  T  G  V  F  M  T  N  F
          TTATAGATGTTAATGAGGAGTATACAGAAGCATCGGCCGTTACAGGAGTATTTATGACTAACTTT

S  M  V  Y  R  T  K  V  Y  I  N  H  P  F  M  Y  M  I  K  D  N  T
          TCGATGGTATATCGTACGAAGGTCTACATAAACCATCCATTCATGTACATGATTAAAGACAACAC

G  R  I  L  F  I  G  K  Y  C  Y  P  Q   -
                  ******
          AGGACGTATACTTTTTATAGGGAAATACTGCTATCCGCAATAAATATAAACAAATAGACTTTTAT

CACGTTTATCTATGTCTAAATATTACAAAT
```

FIGURE 2A-1

```
GTTAAGTATGAATACGGGGTACAAACATAAACTGAAGTTTAACATTATTTATTTATGATATATAT

40►M  D  I  F  K  E  L  I  L  K  H  T  D  E  N
CGTTATTGTTTGGTCTATACCATGGATATCTTTAAAGAACTAATCTTAAACACACGGATGAAAA

V  L  I  S  P  V  S  I  L  S  T  L  S  I  L  N  H  G  A  A  G
TGTTTTGATTCTCCAGTTTCTATTTTATCTACTTTATCTATTCTAAATCATGGAGGAGCTGGTT

S  T  A  E  Q  L  S  K  Y  I  E  N  M  N  E  N  T  P  D  D  N
CTACAGCTGAACAACTATCAAAATATATAGAGAATATGAATGAGAATACACCCGATGACAATAAT

D  M  D  V  D  I  P  Y  C  A  T  L  A  T  A  N  K  I  Y  G  S  D
GACATGGACGTAGATATTCCGTATTGTGCGACACTAGCTACCGCAAATAAATATACGGTAGCGA

S  I  E  F  H  A  S  F  L  Q  K  I  K  D  D  F  Q  T  V  N  F
TAGTATCGAGTTCCACGCCTCCTTCCTACAAAAGATTTCAAACTGTAAACTTTA

N  N  A  N  Q  T  K  E  L  I  N  E  W  V  K  T  M  T  N  G  K  I
ATAATGCTAACCAAACAAGGAACTAATCAACGATTGGGTTAAGACAATGACAAATGGTAAAATT
```

FIGURE 2A-2

```
N  S  L  L  T  S  P  L  S  I  N  T  R  M  T  V  V  S  A  V  H  F
AATTCCTTATTGACTAGTCCGCTATCCATTAATACTCGTATGACAGTTGTTAGCGCCGTCCATTT

K  A  M  W  K  Y  P  F  S  K  H  L  T  Y  T  D  K  F  Y  I  S
TAAAGCAATGTGGAAATATCCATTTTCTAAACATCTTACATATACAGACAAGTTTTATATTCTA

K  N  I  V  T  S  V  D  M  M  V  S  T  E  N  N  L  Q  Y  V  H  I
AGAATATAGTTACCAGTGTTGATATGGTGAGCACTGAGAATAACTTGCAATATGTACATATT

N  E  L  F  G  G  F  S  I  I  D  I  P  Y  E  G  N  S  S  M  V  I
AATGAATTATTCGGAGGATTCTCTATTATCGATATTCCATACGAGGAAACTCTAGTATGGTAAT

I  L  P  D  D  I  E  G  I  Y  N  I  E  K  N  I  T  D  E  K  F
TATACTACCGGACGACATAGAAGGTATATATAACATAGAAAAAATATAACAGATGAAAAATTTA

K  K  W  C  G  M  L  S  T  K  S  I  D  L  Y  M  P  K  F  K  V  E
AAAAATGGTGTGTGGTATGTTATCTACTAAAAGTATAGACTTGTATATGCCAAAGTTTAAAGTGGAA
```

FIGURE 2A-3

```
  M   T   E   P   Y   N   L   V   P   I   L   E   N   L   G   L   T   N   I   F   G   Y
ATGACAGAACCGTATAATCTGGTACCGATTTTAGAAAATTTAGGACTTACTAATATATTCGGATA

Y   A   D   F   S   K   M   C   N   E   T   I   T   V   E   K   F   L   H   T   T
TTATGCAGATTTTAGCAAGATGTGTAATGAAACTATCACTGTAGAAAAATTTCTACATACGACGT

F   I   D   V   N   E   E   Y   T   E   A   S   A   V   T   G   V   F   M   T   N   F
TTATAGATGTTAATGAGGAGTATACAGAAGCATCGGCCGTTACAGGAGTATTTATGACTAACTTT

S   M   V   Y   R   T   K   V   Y   I   N   H   P   F   M   Y   M   I   K   D   N   T
TCGATGGTATATCGTACGAAGGTCTACATAAACCATTCATGTACATGATTAAAGACAACAC

G   R   I   L   F   I   G   K   Y   C   Y   P   Q   -
              ******
AGGACGTATACTTTTTATAGGGAAATACTGCTATCCGCAATAAATATAAACAAATAGACTTTTAT

CACGTTTATCTTATGTCTAAATATTACAAAT
```

FIGURE 3A-1

>XHHU3 --- ANTITHROMBIN-III PRECURSOR - HUMAN    71,  366
27.2% IDENTITY IN 294 AA OVERLAP

```
XHHU3   MYSNVIGTVTSGKRKVYLLSLLLIGFWDCVTCHGSPVDICTAKPRDIPMNPMCIYRSPEK
                10        20        30        40        50        60
                                                     10
GENEI                                        MDIFKELILKHTDENVLI

XHHU3   KATEDEGSEQKIPEATNRRVWELSKANSRFATTFYQHLADSKNDNDNIFLSPLSISTAFA
                70        80        90       100       110       120
         20        30        40        50        60        70
GENEI   SPVSILSTLSILNHGAAGSTAEQLSKYIENMNENTPDDNNDMDVDIPYCATLATANKIYG

XHHU3   MTKLGACNDTLQQLMEVFKFDTISEKTSDQIHFFFAKLNCRLYRKANKSSKLVSANRLFG
               130       140       150       160       170       180
         .: :   :  .  :  :   .    .::.:::  :.::   ::.: ::  : :   :
         80        90       100       110       120       130
GENEI   SDSIEFHASFLQKIKDDF----QTVNF-NNANQTKELINEWVKTMTNGKINSLLTS-PLS
         . :: . :     :      . :: :      :  ::    : :   :   :
XHHU3   DKSLTFNETYQDISELVYGAKLQPLDFKENAEQSRAAINKWVSNKTEGRITDVIPSEAIN
               190       200       210       220       230       240
```

FIGURE 3A-2

```
              140        150        160        170        180        190
GENEI  INTRMTVVSAVHFKAMWKYPFSKHLTYTDKFYISKNIVTSVDMMVSTENNLQYVHINELF
       :  ::::::  ::  ::X::   ::  :: :: :::: ::  ::::  ::::  ::X
XHHU3  ELTVLVLVNTIYFKGLWKSKFSPENTRKELFYKADGESCSASMMY-QEGKFRYRRVAE--
              250        260        270        280        290

200        210        220        230        240        250
GENEI  GGFSIIDIPYEGNS-SMVIILPDDIEGIYNIEKNITDEKFKKWCGMLSTKSIDLYMPKFK
       : :::::: ::     ::::: :::::  ::::  :::::: ::: ::::::
XHHU3  -GTQVLELPFKGDDITMVLILPKPEKSLAKVEKELTPEVLQEWLDELEEMMLVVHMPRFR
              300        310        320        330        340        350

260        270        280        290        300
GENEI  VEMTEPYNLVPILENLGLTNIF-----GYYADFSKMCNETITVEKFLHTTFIDVNEEYTEA
       ::  ::::: :  :::  :::      :::  :::  ::::::: :: ::::::::::
XHHU3  IE--DGFSLKEQLQDMGLVDLFSPEKSKLPGIVAEGRDDLYVSDAFHKAFLEVNEEGSEA
              360        370        380        390        400        410

310        320        330        340        350
GENEI  SAVTGVFMTNFSM-VYRTKVYINHPFMYMIKDNT-GRILFIGKYCYPQ
       ::::::  ::  ::  ::  :  ::   ::::  :::::
XHHU3  AASTAVVIAGRSLNPNRVTFKANRPFLVFIREVPLNTIIFMGRVANPCVK
              420        430        440        450        460
```

FIGURE 3A-3

GENE I
ALPHA-1-ANTICHYMOTRYPSIN PRECURSOR - HUMAN

```
 90  QYGSEA KDDFATQFDVDNFFNDNNSANQNAATKAKEK**E
161  *****  *    *   *  *   *   *   *   *  *

110  LINEWYDKTMTNGTRGKINSLLTSLLKD*
179  L    *  *      *   *   *  **

130  PLSINTQDSKRMTMMTVLVNYSAVHFKINSLLTSMW
199  PD*  * *  *    *  *    *   KIT DLI  *

150  KYPFSKHLYT DKFYISKNIKAMW
218  EMP FDQ THQS RFFYL KK AKW

170  VTSVDMMMVSTHENNLQYVHIN*
238  WVMPMMS LHHH TIPYFRD   
                          E

190  ELFGGFSIDIPYEGN SMVL*
258  ELSCTVELK YTG NASAL  
```

(Aligned protein sequences; positions labeled 90/161, 110/179, 130/199, 150/218, 170/238, 190/258)

GENE I
ALPHA-1-ANTICHYMOTRYPSIN PRECURSOR - HUMAN

MATCHES = 124     LENGTH = 368     MATCHES/LENGTH = 33.7 PERCENT

GENE I
ALPHA-1-ANTITRYPSIN - BABOON

```
258  YNLVPILENLGLTNIFGYYA
312  YDL*VLGHLGIT*KVFSNGA*

278  DFSKMCNETITVEKFLHTT
332  DLSGVTEDAPLKLSKAVHKA*

297  FIDVNEEYTEASAVTGVFMT
352  VLT*IDEKGTEA*AGAM*FLE*

317  NFSMVYRTKVYINHPFMY M
370  AIPMSIPPEVKFNKPFVFLM*

336  IKDNTGRILFIGKYCYP  352
390  IEQNTKSPLFIGKVVNP*  406
```

MATCHES = 76    LENGTH = 257    MATCHES/LENGTH = 29.6 PERCENT

FIGURE 3A-9

GENE I
ALPHA-1-ANTITRYPSIN PRECURSOR - HUMAN

MATCHES = 80        LENGTH = 261        MATCHES/LENGTH = 30.7 PERCENT

GENE I
GENE X PROTEIN - CHICKEN (FRAGMENT)

MATCHES = 73    LENGTH = 237    MATCHES/LENGTH = 30.8 PERCENT

FIGURE 3A-14

GENE I
GENE Y PROTEIN (OVALBUMIN-RELATED) - CHICKEN

```
196  SIHIDIPYEASGNDSSMVILPD
230   * ILELPYA*GDLSMLVLLPD

215  DIEGIYNIEKIHNITDEKFKKW
249  EVSGLERI*KTINFDKLREW*

235  CGMLSTKKSIDLYMPKFKV*
269  TTNAMAKKS*MKVYLPRMKI

253  EMTEPYNLVPILENLGLTNII
289  E*EKYNLTSILMAGMTDL*

273  FGYYADFNLTGISSVDCNETITVD*
307  FSRSANLT*GIDNLMISD*

290  EKFLHTTFIDVNEEYTEASA*
327   AV*HGVFMEVNEEGTEATG*
```

MATCHES = 93    LENGTH = 264    MATCHES/LENGTH = 35.2 PERCENT

FIGURE 3B-1

GENE II
ALPHA-1-ANTICHYMOTRYPSIN PRECURSOR - HUMAN

MATCHES = 79       LENGTH = 223       MATCHES/LENGTH = 35.4 PERCENT

FIGURE 3B-3

GENE II
ALPHA-1-ANTITRYPSIN - BABOON

MATCHES = 82    LENGTH = 258    MATCHES/LENGTH = 31.8 PERCENT

GENE II
ALPHA-1-ANTITRYPSIN PRECURSOR - HUMAN

MATCHES = 83    LENGTH = 261    MATCHES/LENGTH = 31.8 PERCENT
```

FIGURE 3B-8

GENE II
ANTITHROMBIN-III PRECURSOR - HUMAN

| 190/306 | 209/326 | 229/346 | 246/366 | 264/386 | 283/404 |
|---|---|---|---|---|---|
| E A * | A E * | E * | G G | T A * | S I * |
| L L | E E | N K * | T P * | K K | V V |
| G S * | M L * | Y L * | S L * | H H | L V * |
| D K * | S E * | S S | G K * | I  * | A A |
| I E | N D * | F * | F S * | M F * | C  * |
| N P * | C L * | G G | V K * | A A | T T |
| D K * | W W | D * | E E | D D | A S * |
| P P | K E * | T E * | T P * | V  * | A A |
| L L | K Q * | V I * | L S * | S S | A A |
| I H | F L * | K R * | G F * | V V | A A |
| V L * | N V * | F F | S L * | Y * | E E |
| V V | T E * | K R * | K D * | D L * | T S * |
| M M | D P * | P P | V V | S D * | Y G * |
| I * | T T | H M * | L L | N D * | E E |
| S I * | L L | H H | G * | C R * | E E |
| T D * | N E * | V V | T M * | M G * | N N |
| D D | Q K * | D V * | D D | N E * | V V |
| G G | E E | I L * | Q * | S A * | D E * |
| V K * | I V * | F M * | L L | Y V * | I L * |
| Y F * | S K * | T M * | Q * | D I * | Y F * |

FIGURE 3B-10

```
303  D C A S T I T N E   F C V D H P F I Y
423  A G R S L N P N R V T F K A N R P F L V
                                              *
321  V I R H V D G K   I L F V G R Y C S P  338
443  F I R E V P L N T   I H I F M G R V A N P  461
                                              *
MATCHES = 95      LENGTH = 279      MATCHES/LENGTH = 34.1 PERCENT

GENE II
GENE X PROTEIN - CHICKEN FRAGMENT

| 170 | 190 | 209 | 227 | 247 | 263 |
|---|---|---|---|---|---|
| 62 | 79 | 99 | 119 | 139 | 159 |

MATCHES = 80    LENGTH = 237    MATCHES/LENGTH = 33.8 PERCENT

GENE II
GENE Y PROTEIN (OVALBUMIN-RELATED) - CHICKEN

MATCHES = 94    LENGTH = 250    MATCHES/LENGTH = 37.6 PERCENT
                                        338
                                        388
```

GENE ENCODING SERINE PROTEASE INHIBITOR

The present invention is related generally to the identification and characterization of new genes and proteins. More particularly, the present invention is related to the identification of genes which encode proteins having substantial degree of homology to the serine protease inhibitor superfamily. There are no known synthetic or microbial proteins capable of specifically inhibiting serine proteases.

SUMMARY OF THE INVENTION

It is, therefore, an object of the present invention to provide isolated, substantially pure, novel serine protease inhibitors.

It is another object of the present invention to provide a nucleotide sequence directing the synthesis of novel serine protease inhibitor, when cloned in a suitable expression vector.

It is a further object of the present invention to provide a therapeutic composition and method for treating or controlling conditions that would benefit from inhibition of serine proteases or that result from the deficiency of serine protease inhibitors, such as emphysema, cirrhosis, liver cancer and the like.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 2A (parts 1-3) and 2B show the nucleotide sequence of the genes I and II, respectively, of vaccinia virus (WR strain) in 5'-3' direction. The predicted coding sequence starting with the initiation codon ATG to the termination codon has been translated into the corresponding amino acid sequence which is shown below or above the nucleotide sequence in the single letter code. The nucleotide sequence was determined by the standard dideoxy-chain termination technique using denatured plasmids as templates and specific oligonucleotides as primers.

FIGS. 3A (parts 1-16) and 3B (parts 1-14) present the alignment of the deduced amino acid sequence of the genes I and II, respectively, of vaccinia virus with some of the members of the serine protease inhibitor superfamily. Members of the superfamily with significant similarities include human plasma serine protease (protein C) inhibitor, human placental plasminogen activator and human beta-migrating plasminogen activator. Dissimilar amino acids have been highlighted by asterisks (*). Gaps imposed to maximize alignment are indicated by empty spaces. The similarity was found by searching the National Biomedical Research Foundation (NBRF) protein data bank using the Beckman Instruments microgenie program.

DETAILED DESCRIPTION OF THE INVENTION

Figure 1:
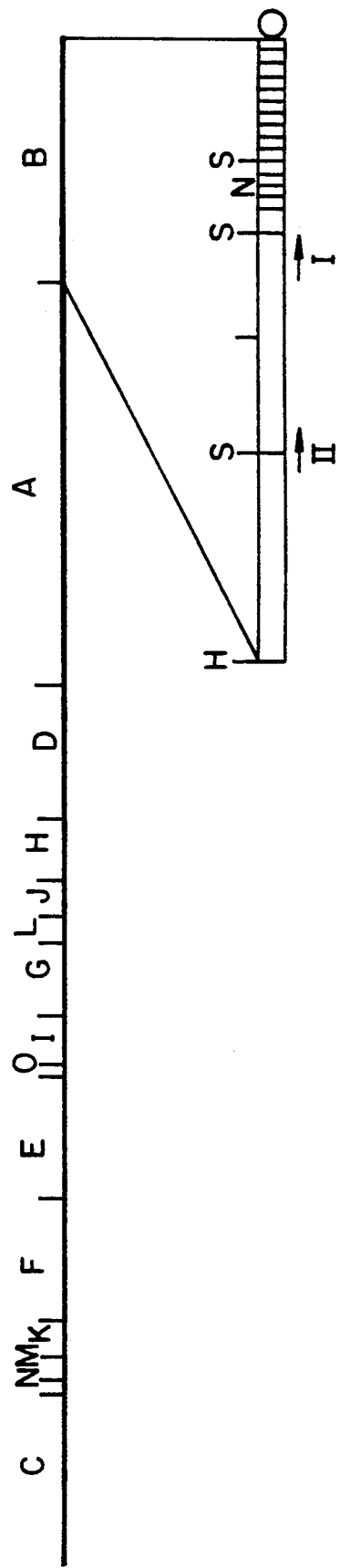
FIG. 1 shows Hind III map of the vaccinia WR strain with the enlarged right end. The vertical bars indicate the inverted terminal repeats. The arrows indicate the direction and the position of the 2 genes, numbered as I and II with similarities to the serine protease inhibitor family. The letters H and S indicate the restriction sites Hind III and SalI, respectively.

The above and various other objects and advantages of the present invention are achieved by the constructions having the nucleotide and amino acid sequences as shown in FIGS. 2A and 2B.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

The term "substantial homology" as used herein means having homology greater than 25%.

The term "substantially pure" as used herein means as pure as can be obtained by standard purification techniques.

Cloning of the genes is achieved by standard recombinant genetic methodologies well known to one of ordinary skill in the art.

Given the cloned genes and the amino acid sequence, the proteins can be synthesized by such methods as commercially available peptide synthesizers or by employing suitable expression vectors and the like, all of such methodologies being well known to one of ordinary skill in the art to which this invention belongs. (See for example Maniatis et al, "Molecular Cloning, A Laboratory Manual," Cold Spring Harbor, N.Y.)

A therapeutic composition in accordance with the present invention comprises effective amount of the serine protease inhibitor to inhibit serine protease activity and a pharmaceutically acceptable carrier, if necessary.

A method for treating or controlling a condition resulting from the deficiency of serine protease inhibitor or that would benefit from inhibition of a serine protease comprises administering to a subject afflicted with said condition, an effective amount of the serine protease inhibitor to alleviate the deficiency of said inhibitor.

A deposit of the embodiments of the present invention has been made at the ATCC on Dec. 16, 1988. The deposit shall be viably maintained, replacing if it becomes non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit (accession numbers 67864 and 67865).

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A cloned gene having the nucleotide sequence of FIG. 2A.

2. A cloned gene having the nucleotide sequence of FIG. 2A and deposited at the ATCC under accession number 67864.

* * * * *